(12) United States Patent
MacHattie et al.

(10) Patent No.: US 7,938,935 B2
(45) Date of Patent: May 10, 2011

(54) INFRARED MEASUREMENT OF PAPER MACHINE CLOTHING CONDITION

(75) Inventors: Ross K MacHattie, Mississauga (CA); Frank M Haran, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 742 days.

(21) Appl. No.: 11/974,093

(22) Filed: Oct. 11, 2007

(65) Prior Publication Data
US 2009/0095432 A1    Apr. 16, 2009

(51) Int. Cl.
*D21F 7/06* (2006.01)
(52) U.S. Cl. ........... 162/198; 162/DIG. 6; 162/DIG. 10; 73/159
(58) Field of Classification Search ................. 162/198, 162/199, 262, 263, 272, 274–279, DIG. 4, 162/DIG. 6, DIG. 10; 700/129; 250/339.1; 73/37.7, 38, 159
See application file for complete search history.

(56) References Cited

U.S. PATENT DOCUMENTS

| | | | |
|---|---|---|---|
| 5,403,447 A | 4/1995 | Jarvinen et al. | |
| 5,820,731 A | 10/1998 | Soderholm | |
| 6,004,429 A | 12/1999 | Schiel | |
| 6,254,726 B1 * | 7/2001 | Steiner et al. | 162/198 |
| 6,706,149 B2 * | 3/2004 | Dick et al. | 162/198 |
| 6,716,316 B2 * | 4/2004 | Grabscheid et al. | 162/199 |
| 6,849,851 B2 * | 2/2005 | Komulainen et al. | 250/340 |
| 2004/0129398 A1 * | 7/2004 | Munch et al. | 162/198 |
| 2005/0103095 A1 * | 5/2005 | Ulfert et al. | 73/38 |
| 2005/0145359 A1 | 7/2005 | Ischdonat et al. | |
| 2006/0109519 A1 | 5/2006 | Beselt et al. | |
| 2007/0151690 A1 | 7/2007 | MacHattie | |

FOREIGN PATENT DOCUMENTS

| | | |
|---|---|---|
| CA | 2278302 A1 | 8/1998 |
| CA | 2606768 A1 | 11/2006 |
| WO | WO 02/052251 A1 | 7/2002 |

OTHER PUBLICATIONS

Smook, Gary A., Handbook for Pulp & Paper Technologists, Angus Wilde Publications, 1992, pp. 256-259.*

* cited by examiner

*Primary Examiner* — Eric Hug
(74) *Attorney, Agent, or Firm* — Cascio Schmeyer & Zervas

(57) ABSTRACT

Infrared spectroscopy techniques are employed to measure (i) the moisture level in both the sheet of wet stock and the papermaking machine clothing on which the sheet is supported and (ii) the moisture level in the clothing alone as a separate layer of material. Differential measurement thus yields the moisture content of the sheet of wet stock alone. Changes in the moisture level in the clothing at the press section can be correlated with corresponding changes in the quality or physical property of the paper produced. Both fixed point and scanning IR sensors are strategically positioned in the press section to generate machine direction and/or cross machine direction water profiles for process control.

13 Claims, 2 Drawing Sheets

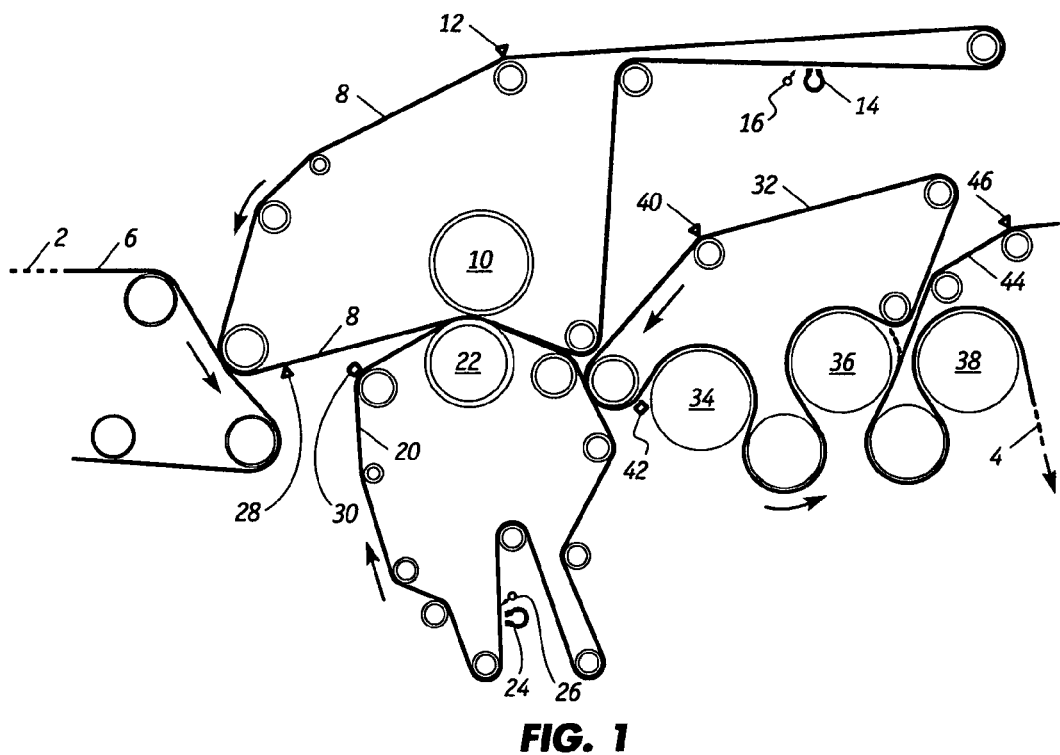
FIG. 1
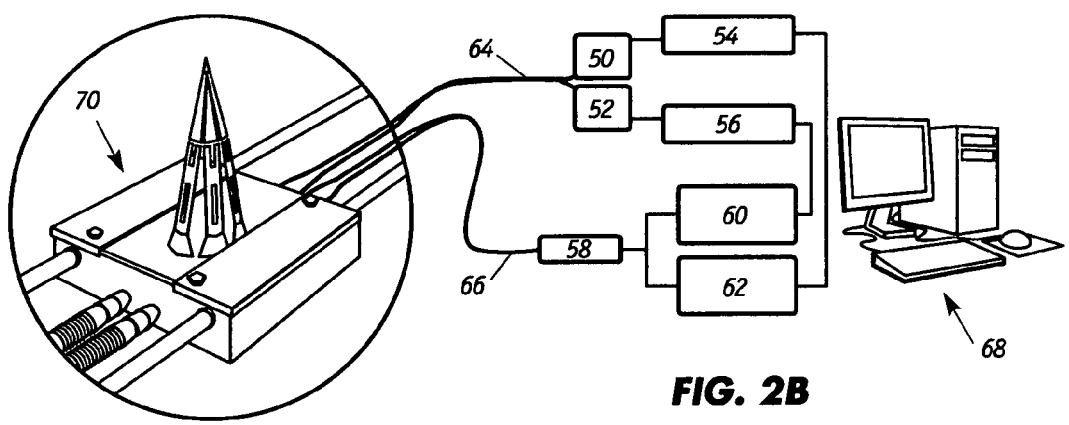
FIG. 2A
FIG. 2B

INFRARED MEASUREMENT OF PAPER MACHINE CLOTHING CONDITION

FIELD OF THE INVENTION

The invention relates generally to condition monitoring and control of papermaking machine clothing and particularly to methods of using infrared measurement techniques to measure and control the water content of press felts, dryer felts, and paper products at different stages of the papermaking process.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. After being dried, the paper is often run between drums which impart the desired smoothness. This process is referred to as calendering. The paper is then typically rolled into a jumbo roll at the reel, the end of the paper machine. Traditionally the quality of the paper is measured by a quality control system having sensors that are typically located just before the reel of the papermaking machine. By measuring the water content in the paper so late in the papermaking process, it is difficult to identify and correct the source of quality problems.

Papermaking machine press fabric, which is commonly referred to as "press felts" or "clothing," plays a dual role in pressing operations. It supports and conveys the paper web of wet stock through the various operations and assists in paper web dewatering. It also acts as a transmission belt to drive other components of the press section. Similarly, dryer felts support the web in the dryer section of the papermaking machine. The typical press fabric run includes tensioning and positioning rolls and includes means to condition and dewater the felt to keep it permeable and open. A variety of mechanical and/or chemical conditioning treatments are used. Most systems utilize hydraulic energy (in the form of high- and low-pressure showers) as the primary means to loosen and flush out fines and fillers from the fabric structure. Following the showering treatments, the fabric is dewatered either by a suction box or a "wringer press." If hydraulic energy by itself is insufficient, detergents and/or chemicals that serve as solvents and cleaning agents can be added.

Even when clothing is properly conditioned and maintained, the dewatering characteristics of the press felt and dryer felt change with time during normal operations of a papermaking machine. This is caused by normal wear on the fabric, especially if the wear is not uniform, and by the presence of excessive dirt which is not removed by conditioning. To compensation for fluctuations in dewatering characteristics, other machine variables can be manipulated to keep the paper web's quality within specification. Indeed, even new fabrics usually undergo a break-in period, during which time the papermaking machine cannot be operated at maximum speeds, before the fabric reaches an acceptable operating condition. Eventually, the fabric must be replaced due to excessive wear or compaction.

The principle technique for monitoring felts uses microwaves to measure the absolute level of water and to generate machine direction (MD) time trends and cross machine direction (CD) profiles of the water in the felts. The measurement is typically performed by a skilled operator who presses a sensor against the edge of a moving felt as he walks across the width of the felt. The recorded readings yield a profile of the moisture distribution.

The shortcomings to this monitoring process which relies on the manual dexterity and skills of an individual are obvious. Aside from the costs, inconsistencies, inherent physical limitations and dangers involved, no accurate "real time" data are generated for process control.

The art is in need of a precise and accurate automatic papermaking machine clothing monitoring system which can be employed to detect real time changes in the physical characteristics of the clothing which in turn can be employed to adjust machine operating parameters to compensate for the changes.

SUMMARY OF THE INVENTION

The present invention is based in part on the recognition that infrared (IR) spectroscopy could accurately measure (i) the water content that is present in both the sheet of wet stock and the papermaking machine clothing on which the sheet of wet stock is supported at the press section, and (ii) the water content in the clothing alone as a separate layer of material. With the invention, changes in the water level in the clothing at the press section can be correlated with corresponding changes in the quality or physical property of the paper produced. In this regard, the information that is derived from the IR measurements allows the condition of the press felts and dryer felts to be monitored and controlled which ultimately result in more consistent and higher quality paper products.

In one aspect, the invention is directed to a process to monitor characteristics of a continuously circulating machine clothing during the manufacture of paper material which includes the steps of:

(a) operating the continuously circulating machine clothing, which has opposed major surfaces including an inner surface and outer surface, such that a sheet of aqueous fibrous composition is supported on a portion of the outer surface of the circulating machine clothing;

(b) irradiating a target area of the circulating machine clothing, wherein the target area is located at a part of the circulating machine clothing that is not supporting the aqueous fibrous composition, with infrared radiation;

(c) detecting the amount of radiation that emerges from the target area of the circulating machine clothing; and (d) developing a machine clothing profile based on the amount of radiation that is detected.

In another aspect, the invention is directed to a process to condition a continuously circulating press felt during the manufacture of paper material, which includes the steps of:

(a) operating the continuously circulating press felt, which has opposed major surfaces including an inner surface and outer surface, such that a sheet of aqueous fibrous composition is supported on a portion of the outer surface of the circulating press felt;

(b) irradiating a target area of the circulating press felt, where the target area is located in a part of the circulating press felt that is not supporting a sheet of aqueous fibrous composition, with infrared radiation;

(c) detecting the amount of radiation that emerges from the target area;

(d) generating signals that are indicative of the water content in the press felt; and (e) subjecting the circulating press felt to selective cleaning and/or vacuuming in response to the signals.

In a further aspect, the invention is directed to a method of controlling the production of paper material wherein a sheet of wet stock comprising fibers is initially formed on a water permeable moving wire of a forming section of a de-watering machine and thereafter a sheet of the web stock is transferred to a press section of the de-watering machine, wherein the press section comprises at least one continuously circulating press felt which has opposed major surfaces including an inner surface and outer surface, which method includes the steps of:

(a) operating the continuously circulating press felt such that a sheet of wet stock is supported on a portion of the outer surface of the circulating press felt;

(b) irradiating a first target area which is on the circulating press felt, wherein the first target area is located at a part of the circulating press felt that is not supporting a sheet of wet stock, with infrared radiation;

(c) detecting the amount of radiation that emerges from the first target area of the circulating press felt;

(d) generating first signals that are indicative of the moisture content in the circulating press felt;

(e) irradiating a second target area which is on a sheet of wet stock that it is supported by the circulating press felt with infrared radiation having a predetermined wavelength that is sensitive to water in both the sheet of wet stock and circulating press felt;

(f) detecting the amount of radiation that emerges from the second target area;

(g) generating second signals that are indicative of the moisture content in both the sheet of wet stock and the circulating press felt;

(h) determining the moisture content in the sheet of wet stock alone and generating third signals that are indicative of the moisture content in the sheet of wet stock alone; and (i) adjusting at least one operating parameter of the de-watering machine in response to the third signals.

BRIEF DESCRIPTION OF THE DRAWINGS

FIG. 1 is a side view of a schematic diagram of a press arrangement in a papermaking machine;

FIGS. 2A and 2B are schematic diagrams of a sensor system; and

DESCRIPTION OF PREFERRED EMBODIMENTS

Figure 3:
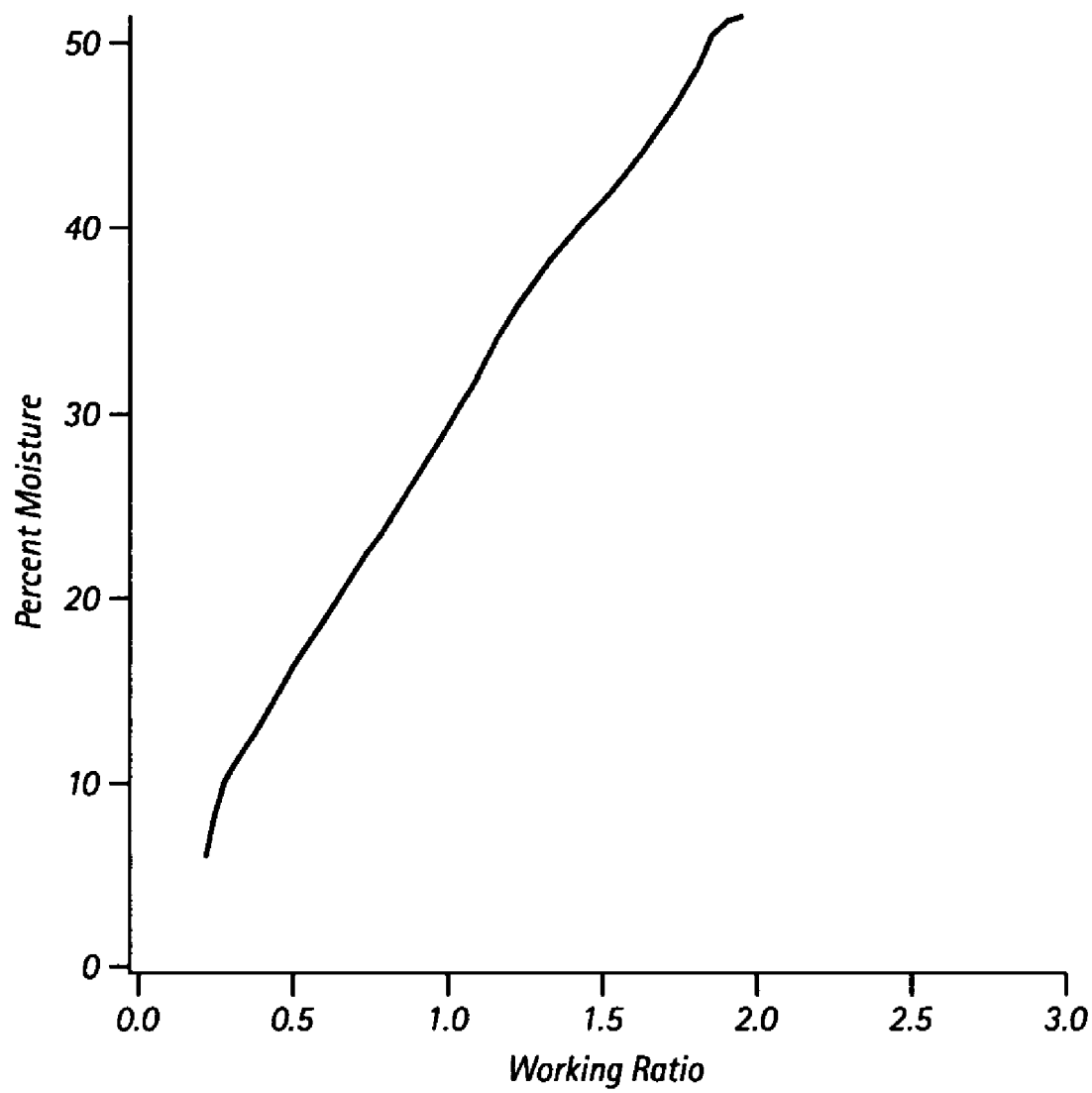
FIG. 3 is a graph of typical IR sensor responses that were obtained from a press felt sample with varying moisture levels.

FIG. 1 depicts a press section which is situated between the end of the forming section and beginning of the dryer section in a papermaking machine. Moisture detecting sensors are strategically positioned to monitor the moisture content of the machine clothing and of the sheet of wet stock and partially de-watered wet stock as the sheet advances through the press section. One feature of the invention is that by identifying potential sources of paper defects early at the press section, corrective actions can be initiated before influences by other machine elements prevent or complicate the identification of the sources of the defects.

As shown in FIG. 1, the press section is a labyrinth, consisting of a number of cooperating endless circulating loops, through which a sheet of wet stock is transformed into a sheet of partially de-watered wet-stock. This exemplary press arrangement includes three separate closed loops that include: (1) upper press felt 8, (2) lower press felt 20, and (3) dryer felt 32. Press felts 8 and 20 function as reservoirs to collect (absorb) water from the sheet of wet stock by pressing and capillary action. The forming wires, press felts, and dryer felts are commonly referred to as papermaking clothing. Dryer felt 32 is heated and water evaporates from the partially de-water wet stock as it is carried by the dryer felt.

Referring to FIG. 1, a sheet of aqueous wet stock 2, with approximately 10-20 percent fiber, is transported from wire 6 of the forming section onto the wet-press section. Specifically, the sheet of wet stock 2 is transferred by suction to the bottom side of upper press felt 8 and is thereafter retained and supported by surface tension on the upper press felt 8 as the sheet becomes disposed between the upper press felt 8 and the lower press felt 20. The sheet of wet of stock, which is sandwiched between the two felts, advances toward a press nip that is created by press rolls 10 and 22 where compression forces water from the wet stock and into the felts. Upon exiting the wet-press step, the partially de-watered and consolidated sheet, which contains about 50 percent dry content, is transferred onto the first dryer felt 32 which carries and supports the sheet as it passes over dryer cylinders 34 and 36 where some residual water is removed by evaporation. The sheet is then transferred onto the second dryer felt 44 which is heated by dryer cylinder 38. (Only one dryer cylinder is shown whereas a commercial papermaking machine typically has thirty to sixty.) At this stage in the process, the relatively thin sheet dried paper product 4, which contains about 10 percent moisture, is available for further papermaking processing, such as coating and calendaring, where the moisture content is reduced to about 5 percent.

IR sensors are deployed to monitor the moisture contents in (i) both the sheet of wet stock (or partially dewatered wet stock) and felt combined and (ii) the felt alone. In particular, with regard to upper press felt 8, a fixed (stationary) IR point sensor 12 is positioned along the top side of upper press felt 8 and a fixed IR point sensor 28 is positioned along a bottom side of the upper press felt 8. IR point sensor is configured to measure only the side of the press felt that comes into contact with the sheet of wet stock. A fixed point sensor only generates a time series of data from one area of the moving sheet in the cross direction, it does not yield a CD profile. Fixed point IR sensor 28 serves to directly measure the water content within the upper press felt 8 alone since there no sheet of wet stock at the top side of upper press felt 8. However, at the beginning of the press section, a sheet of wet stock is supported by surface tension along the bottom side of upper press felt 8 so the moisture content that is present in both the sheet of wet stock and upper press felt 8 is simultaneously measured by the fixed point IR sensor 28. It should be noted that the upper press felt 8 at the location of fixed point IR sensor 28 also contains a significant amount of water. As is apparent, by subtracting the water content of the upper press felt 8 from the combined water content for both the upper press felt 28 and sheet of wet stock, this indirect differential measurement provides a good approximation of the water content in the sheet of wet stock itself. Moreover, by monitoring the water content of the sheet of wet stock at the press section, appropriate operating parameters of the papermaking process can be adjusted in response to fluctuations in the water content so that the dried paper 4 exhibit the requisite degree of moisture and other physical attributes.

It has been demonstrated that normal wear on a press felt reduces its capacity to absorb and retain water due to a loss in structural integrity; this capacity is also adversely affected by the presence of debris on the press felt which is normally removed during conditioning of the press felt. One aspect of the invention is that moisture content data for a press felt can be employed to control the conditioning process. For example, with respect to upper press felt 8, the water content signals from fixed point sensor 12 can be employed to (1) control the operations of cleaning section 16 and vacuuming (drying) section 14 in order to maintain the water level in the felt to be within a desired range and/or (2) determine the efficiency of the cleaning and drying equipment for the felt. Methods of conditioning papermaking machine clothing are described in US Patent Application Publication No. 2007/0151690 to MacHattie et al. which is incorporated herein by reference. Furthermore, when the press felt's capacity to retain water decreases to an unacceptable level despite conditioning, then the press felt has reached the end of its useful life and must be replaced.

Similarly, for the lower press felt 20, the water content in the felt is measured by a scanning IR sensor 30 at a location on the felt before it reaches the press nip that is formed by press rolls 10 and 22. Signals from IR sensor 30 can be employed to control the condition process performed by cleaning section 26 and vacuuming section 24.

With regard to the first dryer felt 32, the water content of the felt is measured by a fixed point IR sensor 40 that is located along the upper surface of the circulating felt. In addition, scanning IR sensor 42 measures the moisture content that is present in both the sheet of partially de-watered wet stock and first dryer felt 32 just before the sheet reaches the dryer cylinder 34. Signals generated by IR sensors 40 and 42 can be used in conjunction to, among other things, calculate the moisture level in the sheet of partially de-water wet stock at the location of IR sensor 42.

Finally, with regard to the second dryer felt 44, the moisture level that is present in the felt is monitored by fixed point IR sensor 46.

During operations of the press section, the thickness of a sheet of wet stock can vary along the cross direction of the felt on which the sheet is supported. Indeed, the surface of the felt along the edge might not be in contact with the sheet at all. Furthermore, debris tends to accumulate at the edges which are not adequately cleaned by the conditioning process. Thus, fixed point IR sensors should be positioned sufficiently away from the edge and toward the center of the felt so that debris does not interfere with the measurements. For felts having a width of 4 meters or more, the sensor should be positioned at least about 0.5 meters from the edge. As is apparent, each of fixed point IR sensor 12, 28, 40 and 46 can be placed by multiple IR sensors that are positioned along the cross direction of the felt or by a scanning IR sensor. These arrangements will yield cross direction measurements. With respect to scanning IR sensors, on-line measurements can be readily achieved by mounting an on-line IR sensor that is scanned over the moving sheet of paper and/or felt in the cross direction. Suitable fiber optic scanning mechanisms are described in US Patent Application Publication No. 2006/0109519 to Beselt et al.

Suitable IR sensors for measuring moisture in the present invention are described in US Patent Application Publication 2006/0243931 to Haran et al. which is incorporated herein by reference. FIGS. 2A and 2B illustrate an exemplary IR sensor that is incorporated into a measurement system which includes two super luminescent light emitting diodes (SLED) 50, 52 that are controlled by driver and thermal equalization control circuits 54 and 56, respectively. Light from the two SLEDs is coupled into a single mode fiber 64 which delivers the light to the sensor head 70 which is supported on guide rails on a scanning mechanism. The sensor head 70 re-directs the light to a sheet of wet stock or paper or clothing and captures light that is scattered back from the sheet or clothing and couples that light into a multi-mode fiber 66 that channels the back-scattered light to the detector 58. The detector 58, such as an indium gallium arsenide (InGaAs) detector, is connected to lock-in amplifiers 60 and 62 where signals are demodulated from the two different wavelengths of light that are used. Signals from this measurement circuit as well as other sensors are analyzed by a computer and software system 68. The IR sensor is preferably configured to operate in the reflection mode, as described above. Alternatively, it can operate in the transmission mode where a separate detector is positioned on the opposite side of the wet stock, paper or clothing to capture light that is transmitted. In either case, light which emerges (reflected or transmitted) from the material contains information about the moisture content that is in the paper, fabric or combination of both paper and fabric is analyzed for moisture content.

Typically, one of the two SLEDs emits light at a water absorption peak and the other SLED emits light that is close by in the spectrum but off of the water absorption peak so that it is used as a reference. The two light sources are modulated at different frequencies and the modulated light sources are coupled to a single fiber optic cable. Suitable water sensitive adsorption peaks exist around the 1.4 to 1.6 μm radiation range and the corresponding off the water adsorption peak is in the 1.2 to 1.3 μm radiation range.

It is preferred that sensitive electronics of the measurement system as illustrated in FIG. 2B are located in a remote, stationary area away from the harsh environment of the press section. In this off-machine design, light from the source(s) of IR is channeled to a scanner head via a fiber optic cable and scattered light that is captured by the scanner head is channeled back the detector via the fiber optic cable. In this fashion, only the scanner head and the connecting fiber optic cable moves back and forth along the cross direction as the water moisture measurements are made with the optic scanner. With appropriate calibration, the measurement signals could yield the water content in terms of grams per square meter (gsm) of water weight or in terms of percent moisture or percent dryness.

An IR sensor that was equipped with two SLED light sources, one emitting light at an adsorption wavelength of 1.3 μm and the other emitting light at a reference wavelength of 1.4 μm, was used to monitor the moisture level in a sample of press felt that had been used in a commercial papermaking machine for about one month. A 3.5 in. (8.9 cm)×3.5 in. (8.9 cm) square sample of felt was removed from a part of the edge which was not in contact with the sheet of wet stock. The sample was first washed in a hot water bath, ultrasonically cleaned for 1 hour, washed again, and then dried overnight in a 105° C. oven. The sample weighed 1262.02 gsm. Water was distributed over the sample before it was placed on a weight scale that was positioned within an enclosed chamber. As the sample dried, the gradual decrease in weight was recorded and at the same time, the IR sensor detected light that was reflected from the sample at both absorption and reference wavelengths. The working ratio is the ratio of the intensity of the reflected as measured at the reference wavelength to that measured at the absorption wavelength.

FIG. 3, which is the graph of moisture content vs. working ratio, shows that based on this felt sample, the accuracy of any calibration depends on the range over which a calibration fit is required which depends on the percentage moisture that we expect to see for a particular felt and application. Analysis of the data suggests that the smaller the moisture range for calibration the greater the accuracy.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A process to monitor characteristics of a continuously circulating machine clothing during the manufacture of paper material which comprises the steps of:
   (a) operating the continuously circulating machine clothing, which has opposed major surfaces including an inner surface and outer surface, such that a sheet of aqueous fibrous composition is supported on a portion of the outer surface of the circulating machine clothing;
   (b) irradiating a target area of the circulating machine clothing, wherein the target area is located at a part of the circulating machine clothing that is not supporting the aqueous fibrous composition, with infrared radiation;
   (c) detecting the amount of radiation that emerges from the target area of the circulating machine clothing;
   (d) developing a machine clothing profile based on the amount of radiation that is detected;
   (e) irradiating a part of the sheet of aqueous fibrous composition, that is supported on the continuously circulating machine clothing, with infrared radiation;
   (f) detecting the amount of radiation that emerges from the sheet of aqueous fibrous composition and the circulating machine clothing;
   (g) determining a first moisture content of the aqueous fibrous composition together with that of the circulating machine clothing;
   (h) determining a second moisture content of the circulating machine clothing alone; and
   (i) subtracting the second moisture content from the first moisture content to determine the moisture content in the sheet of aqueous fibrous composition.

2. The process of claim 1 wherein the infrared radiation includes a first wavelength region that is sensitive to water and a second wavelength region that is less sensitive to water.

3. The process of claim 1 wherein step (c) comprises detecting the amount of radiation that is reflected from the target area or transmitted through the clothing.

4. The process of claim 1 wherein the machine clothing profile comprises a moisture content machine direction profile or a moisture content cross machine direction profile.

5. The process of claim 1 wherein step (b) comprises irradiating along a cross direction that is perpendicular to the circulating machine clothing direction such that step (c) comprises detecting the amount of radiation that emerges along a cross direction of the circulating machine clothing.

6. The process of claim 5 wherein step (b) employs an infrared measuring device which is scanned back and forth along the cross direction.

7. The process of claim 1 wherein step (b) irradiating a target area of the clothing with a fixed point infrared measuring device.

8. A method of controlling the production of paper material wherein a sheet of wet stock comprising fibers is initially formed on a water permeable moving wire of a forming section of a de-watering machine and thereafter a sheet of partially de-watered wet stock is transferred to a press section of the de-watering machine, wherein the press section comprises at least one continuously circulating press felt which has opposed major surfaces including an inner surface and outer surface, which method comprises the steps of:
   (a) operating the continuously circulating press felt such that a sheet of partially de-watered wet stock is supported on a portion of the outer surface of the circulating press felt;
   (b) irradiating a first target area which is on the circulating press felt, wherein the first target area is located at a part of the circulating press felt that is not supporting a sheet of partially de-watered wet stock, with infrared radiation;
   (c) detecting the amount of radiation that emerges from the first target area of the circulating press felt;
   (d) generating first signals that are indicative of the moisture content in the circulating press felt;
   (e) irradiating a second target area which is on a sheet of partially de-watered wet stock that it is supported by the circulating press felt with infrared radiation;
   (f) detecting the amount of radiation that emerges from the second target area;
   (g) generating second signals that are indicative of the moisture content in both the sheet of partially de-watered wet stock and the circulating press felt;
   (h) determining the moisture content in the sheet of partially de-watered wet stock alone and generating third signals that are indicative of the moisture content in the sheet of partially de-watered wet stock alone; and
   (i) adjusting at least one operating parameter of the de-watering machine in response to the third signals.

9. The method of claim 8 wherein step (b) comprises irradiating along a cross direction that is perpendicular to the circulating press felt direction such that step (c) comprises detecting the amount of radiation that emerges along the cross direction of the first target area, and step (e) comprises irradiating along a cross direction that is perpendicular to the circulating press felt such that step (f) comprises detecting the amount of radiation that emerges along the cross direction of the second target area.

10. The method of claim 9 further comprising the step of developing a moisture profile of the sheet of partially de-water wet stock based on the third signals and step (i) comprises adjusting at least one operating parameter on the basis of the moisture profile.

11. The method of claim 8 wherein in step (b) the infrared radiation includes a first wavelength region that is sensitive to water and a second wavelength region that is less sensitive to water and in step (e) the infrared radiation includes a first wavelength region that is sensitive to water and a second wavelength region that is less sensitive to water.

12. The method of claim 8 wherein step (c) comprises detecting the amount of radiation that is reflected from the first target area or that is transmitted through the press felt and step (f) comprises detecting the amount of radiation that is reflected from the second target area or that is transmitted through sheet of partially de-watered wet stock and press felt.

13. The method of claim 8 wherein step (b) comprises irradiating the first target area with a first fixed point infrared measuring device and step (e) comprises irradiating the second target area with a second fixed point infrared measuring device.

* * * * *